United States Patent [19]

Fox

[11] Patent Number: 5,562,612
[45] Date of Patent: Oct. 8, 1996

[54] APPARATUS AND METHOD FOR REVERSE FLOW IRRIGATION AND ASPIRATION OF INTERIOR REGIONS OF THE HUMAN EYE

[75] Inventor: Martin Fox, New York, N.Y.

[73] Assignee: Charles D. Kelman, New York, N.Y.

[21] Appl. No.: 401,560

[22] Filed: Mar. 9, 1995

Related U.S. Application Data

[63] Continuation-in-part of Ser. No. 383,083, Feb. 2, 1995.

[51] Int. Cl.⁶ .................................................. A61M 1/00
[52] U.S. Cl. .................. 604/27; 604/22; 604/35
[58] Field of Search ............................... 604/22, 27, 28, 604/35, 43, 128

[56] References Cited

U.S. PATENT DOCUMENTS

| | | | |
|---|---|---|---|
| 3,812,855 | 5/1974 | Banko | 128/276 |
| 3,902,495 | 9/1975 | Weiss et al. | 128/276 |
| 4,274,411 | 6/1981 | Dotson, Jr. | 128/276 |
| 4,465,470 | 8/1984 | Kelman | 604/27 |
| 4,764,165 | 8/1988 | Reimals et al. | 604/35 |
| 5,084,012 | 1/1992 | Kelman | 604/35 |
| 5,154,694 | 10/1992 | Kelman | 604/22 |
| 5,417,654 | 5/1995 | Kelman | 604/22 |

*Primary Examiner*—John D. Yasko
*Assistant Examiner*—Laird J. Knights
*Attorney, Agent, or Firm*—Darby & Darby, P.C.

[57] ABSTRACT

A surgical instrument and method for aspirating and irrigating material within a posterior capsule of an eye, including an elongated hollow tube member having a tip portion with a fluid conduit extending therethrough to a region of the tip thereof, a sleeve member surrounding the tube member in a direction of elongation of the tube member so as to define an annular space between the sleeve and the tube member, an irrigation supply for conveying an irrigation fluid through the hollow of the tube member to flow to the region of the capsule to be irrigated, vacuum for aspirating fluid from the interior of the capsule to flow through the annular space, and flow controls to selectively reverse the direction of fluid flow through the irrigation supply and the vacuum so that irrigation and aspiration take place through the annular space and the hollow tube, respectively.

14 Claims, 2 Drawing Sheets

APPARATUS AND METHOD FOR REVERSE FLOW IRRIGATION AND ASPIRATION OF INTERIOR REGIONS OF THE HUMAN EYE

CROSS-REFERENCE TO COPENDING APPLICATION

This is a continuation-in-part of patent application Ser. No. 08/383,083, filed Feb. 2, 1995, entitled "APPARATUS AND METHOD FOR REVERSE FLOW IRRIGATION AND ASPIRATION OF INTERIOR REGIONS OF THE HUMAN EYE".

BACKGROUND OF THE INVENTION

The present invention relates to material removal devices and methods, and more particularly to disintegration and removal of a cataracted lens from a human or animal eye. There are known instruments used in the removal of cataracts having a sleeve and vibratory needle within the sleeve. Irrigation of the interior of the eye is accomplished through the annular space between the sleeve and the needle, while aspiration is carried out through the lumen in the needle.

The vibratory needle assists in the lens tissue disintegration, also known as phaco-emulsification. The cutting along its axis at a very high frequency. The movement of the vibrating cutting tip causes the lens tissue to disintegrate. As the lens breaks apart, the resulting loose lens particles are aspirated from the capsular bag under vacuum through a conduit in the tubular cutting tip of the vibrating instrument.

U.S. Pat. No. 3,589,363 to Banko and Kelman discloses such a hand held instrument for breaking apart and removing tissue from a body site, such as cataracted lens tissue from a human eye.

Conventional systems are known in which irrigation through the hand held instrument operates on a gravity feed principle, e.g., from an irrigation bottle to the annular space between the sleeve and the needle. Such is exemplified in U.S. Pat. No. 4,465,470. In accordance with its teaching, an eye irrigation solution container is arranged at a higher elevation than the eye. A conduit extends downwardly from the container to a drain at an elevation lower than the eye. Gravity flow of fluid from the container to the drain produces a negative pressure in the interior of the needle to aspirate fluid from the eye. Irrigation/aspiration branches extend from the conduit to a conventional irrigation/aspiration hand held instrument. The instrument has an inner needle-like irrigation tube surrounded by an outer sleeve. Fluid flow is from the container through the conduit to the irrigation branch and into the eye through the annular space between the sleeve and the needle. Aspiration flow is from the eye through the human in the needle and through the aspiration branch, back to the conduit and then to the drain.

Alternatively, aspiration may be controlled by a peristaltic or venturi pump, which provides the vacuum to aspirate fluid and lens material. For instance, plugging the aspiration line to eliminate outflow completely would result in a cloud of unaspirated emulsate obscuring the view within the eye. Aspirating such emulsate is therefore desirable. Even without such a peristaltic or venturi pump, outflow from the eye through the lumen in the tip would still occur because the vibrating phaco tip alone acts as a pump.

The use of so-called zero vacuum is conventional during the sculpting phase of a nucleo fractis phaco-emulsification technique. Even with so-called zero vacuum and very low aspiration rates, however, portions of the posterior capsule of the eye can still be attracted to the phaco tip. When emulsifying close to the posterior capsule with a conventional instrument that irrigates through the annular space between the sleeve and needle and aspirates through the lumen of the needle, there is a danger that the capsule may be accidently touched with the aspiration tip of the needle. In that case, the portion of the capsule that is touched may be sucked into the opening of the needle, resulting in breakage of the capsule.

It would therefore be desirable to devise a surgical instrument with which a sculpting phase of a nucleo phaco-emulsification technique avoids attracting the posterior capsule to the phaco tip and actually pushes the capsule away from the vibrating tip.

SUMMARY OF THE INVENTION

The invention is directed to a material removal apparatus and method, particularly one useful for removal of a cataracted lens with a phaco emulsifier, in which attracting the posterior capsule to the phaco tip is avoided by reversing the flow such that irrigation is through the lumen of the needle and aspiration is through the annular spacing between the needle and the outer sleeve.

One aspect of the invention resides in a surgical instrument for aspirating and irrigating material within a lens capsule of an eye, including an elongated hollow tube member having a tip portion with a fluid conduit extending therethrough to a region of the tip thereof, a sleeve member surrounding the tube member in a direction of elongation of the tube member so as to define an annular space between the sleeve and the tube member, irrigation supply for conveying an irrigation fluid through the annular space of the sleeve member to flow to the region of the capsule to be aspirated, vacuum for aspirating fluid from the interior of the capsule to flow through said hollow of the tube member, and flow control means to reverse the irrigation supply and the aspirating vacuum so that irrigation is through the hollow of the tube member and aspiration is through the annular space between the needle and the surrounding sleeve.

BRIEF DESCRIPTION OF THE DRAWING

For a better understanding of the present invention, reference is made to the following description and accompanying drawings, while the scope of the invention is set forth in the appended claims.

DESCRIPTION OF THE PREFERRED EMBODIMENT

Conventional vibratory instruments for the removal of material from the eye have used a handpiece having a straight operative tip at the end thereof. U.S. Pat. No. 3,589,363, which is incorporated herein by reference, discloses an instrument having a handpiece which has an elongated tip at one end. The elongated tip is inserted through an incision made in the cornea. The instrument is capable of vibrating the operative tip at ultrasonic frequencies of variable amplitude and duration to break apart particles of the material, such as a cataracted lens, to be removed.

A source of fluid irrigation and a source of fluid suction are provided respectively at the annular space in the sleeve and at the conduit in the needle, to dispense and withdraw fluid to and from the area in proximity of the material to be removed.

Figure 1:
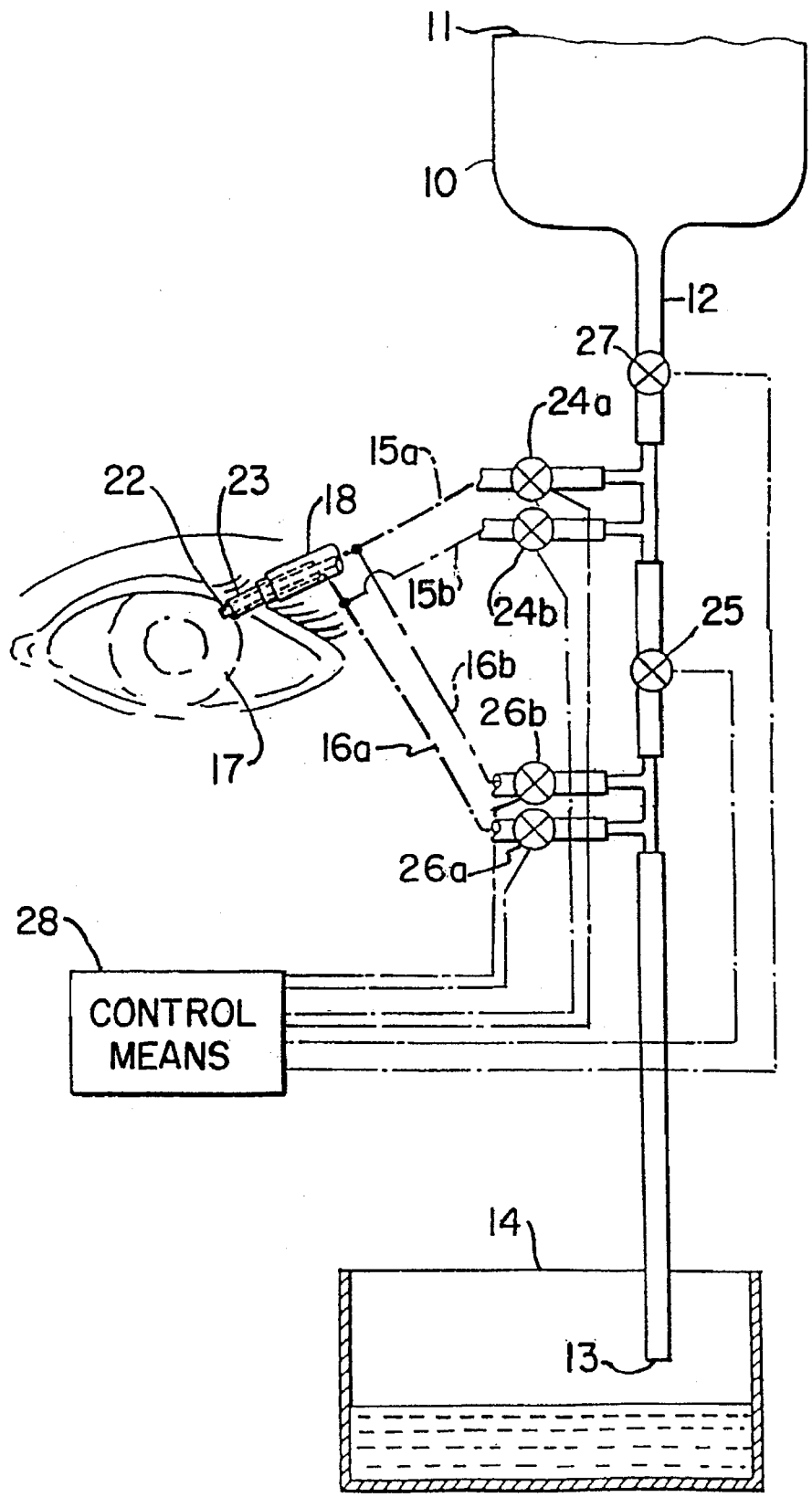
FIG. 1 is a schematic drawing showing an apparatus for irrigating and aspirating an eye, constructed in accordance with an embodiment of the invention.

FIG. 1 illustrates an embodiment of the invention that is a modification of the apparatus disclosed in U.S. Pat. No. 4,465,470, whose contents are incorporated by reference. For the sake of brevity, the following components remain the same as in that disclosure: fluid container 10, irrigation solution 11, fluid conduit 12, open end 13, drain container 14, conduits 15a, 16a (represented by broken lines), conventional irrigation/aspiration hand piece 18, irrigation tip 22, aspiration sleeve 23, first valve means 24a, second valve means 25, third valve means 26a, fourth valve means 27 and control means 28. The eye 17 is also depicted. Each of the valve means may be a conventional solenoid valve, which may be manually operated if so desired.

Unlike the structure disclosed in U.S. Pat. No. 4,465,470 there is, according to the present invention, an additional conduit 15b, that taps into conduit 16a and has its own solenoid valve 24b, which may be manually operated, if desired. Another conduit 16b taps into conduit 15a and has its own solenoid valve 26b, which may also be manually operated, if desired. In addition, the control means 28 regulates the opening and closing of valves 24a, 24b, 26a, 26b such that only two flow conditions are possible for irrigation and aspiration: either valves 24a and 26a are open and valves 24b and 26b are closed, or vice versa.

In this manner, irrigation is through valves 24a or 24b, depending upon which valve is open and aspiration is through valves 26a, 26b, depending upon which is open at any given time.

To irrigate the eye, irrigation may be selected through either conduit 15a or 15b at any one time, but not both. Assuming the former, the control means 28 opens solenoid valve 24a and closes solenoid valve 25 while solenoid valve 27 remains open and solenoid valves 26a, 26b and 24b remain closed. Fluid flows through conduit 12, solenoid valve 27, conduit branch 15a, solenoid valve 24a and tip 22 into the eye 17 under the force of gravity.

On the other hand, if flow through conduit 15b is desired, the same procedure takes place except that solenoid valve 24a is closed and solenoid valve 24b is open so that irrigation flow is through conduit branch 15b instead of conduit branch 15a and through a portion of conduit 16a to sleeve 23 instead of through tip 22.

Figure 2:
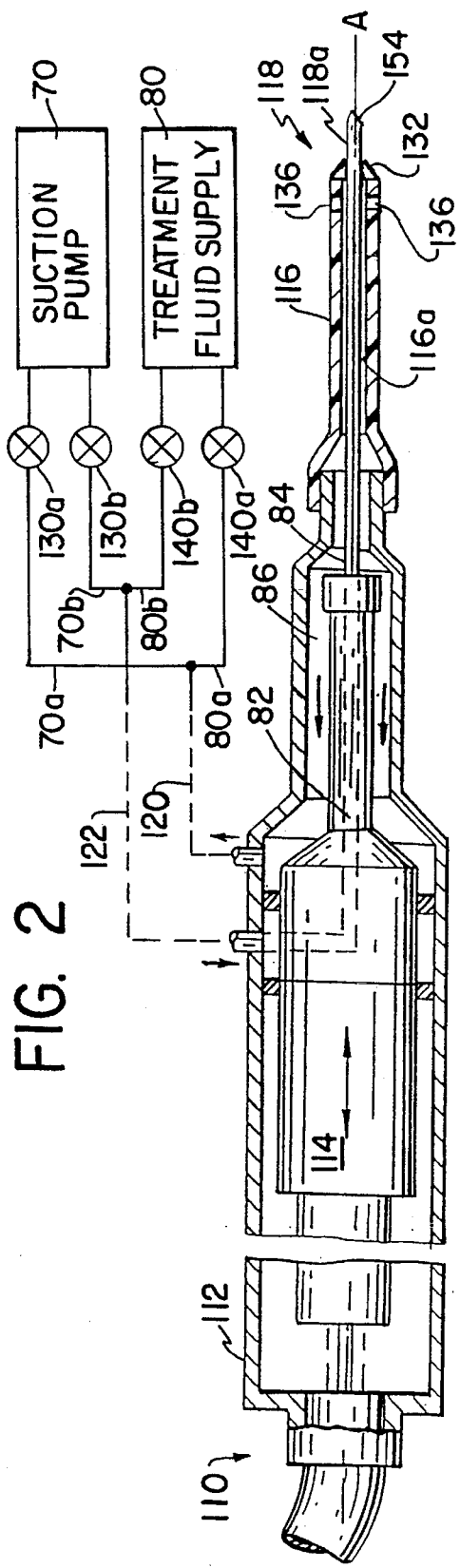
FIG. 2 is a schematic drawing showing an apparatus for irrigating and aspirating an eye, constructed in accordance with another embodiment of the invention.

To irrigate and aspirate the eye through conduit 15a and 16a, respectively, the control means 28 opens solenoid valve 26a while solenoid valves 24a and 27 remain open and solenoid valves 25 and 26b remain closed. Fluid continues to flow into the eye 17 through tip 22 as previously described in connection with irrigation through channel 15a. Fluid then flows out of the eye 17 through radial holes or channels in the sleeve 23 to the annular space between sleeve 23 and tip 22, and then through the conduit branch 16a, the solenoid valve 26a and the conduit 12 to the open end 13 under the force of gravity. The sleeve 23 is provided with radial holes or channels 136, as seen in FIG. 2. According to the preferred embodiment of the invention, the radial holes 136 are of substantially the same diameter as the outside diameter of the tip 22 in the region of the holes 136.

To irrigate and aspirate the eye through conduit 15b and 16b, respectively, the control means 28 opens solenoid valve 26b while solenoid valves 24b and 27 remain open and solenoid valves 24a, 25 and 26a remain closed. Fluid continues to flow into the eye 17 through tip 22 as previously described in connection with irrigation through channel 15b. Fluid then flows out of the eye 17 through the tip 22, the conduit branch 16b, the solenoid valve 26b and the conduit 12 to the open end 13 under the force of gravity.

It is important for the fluid pressure in the eye not to become excessive. By use of the gravity feed and gravity discharge apparatus and method according to this invention, a safe irrigation/aspiration procedure is possible. The surgeon using the apparatus can, by varying the height of the container 10, vary the flow rate of the fluid to the eye and thus vary the fluid pressure in the eye.

When reversing flow, such that irrigation will be through the lumen of needle (via tip 22) rather than through the annular space 116a between the needle and sleeve (via sleeve 23), the velocity of the irrigation stream will increase because the opening of the tip 22 is conventionally much smaller than the end of the annular space between the tip 22 and the sleeve 23. Therefore, the irrigation stream entering the eye through the lumen tip 22 will have a greater pressure than did the irrigation stream entering through the end of the annular space 116a before the flow reversal, unless steps are take to reduce the volumetric flow rate of the irrigation stream reaching the tip 22.

Such reduction may be attained by lowering the height of the fluid container 10 relative to the eye level 17 (because such a gravity feed determines the fluid inflow rate) or by regulating a volumetric flow control valve that is interposed in the conduit 12 upstream of the branch conduits 15a, 15b accordingly and that replaces the solenoid valve 27. Also, the aspiration flow rate must be reduced to balance in and out flows.

Safe inflation of the anterior chamber of the eye during the surgical procedure may be realized by ensuring a proper balance between the in and out flows. Eye surgeons can readily ascertain the extent of inflation through observation of the bulge of the eye and assess whether the extent of inflation is safe for operating based on their training and experience. For instance, the eye surgeon can tell whether the inflation level is too much such that the eye is in danger of overpressurizing. On the other hand, the inflation level can not be so low that the eye essentially is in a collapsed state, because then there would be no room for the surgeon to operate.

The preferred embodiment employs a phaco tip 22 made of titanium with an outside radius r of 0.018725 inches and an inside radius of 0.0125 inches. The tip is cylindrical and concentrically surrounded in its direction of elongation by a silicone sleeve 23. The sleeve preferably has an inside radius R of 0.028 inches. In accordance with the preferred embodiment, the clearance for the fluid flow may be an annular space 116a having a dimension, in radial direction, of approximately 0.007 inches to 0.009 inches. The end of the phaco tip may be straight, beveled or curved. The invention is not intended to be limited to the aforementioned dimensions or materials, but they are mentioned for illustrative purposes.

In accordance with the preferred embodiment employing the phaco tip and sleeve of the previously mentioned dimensions, fluid balance is achieved by maintaining a standard fluid container height or bottle height of 70 cm and reducing the aspiration flow rate to 12–14 cc/minute, with a vacuum limit of 100–110 inches of mercury (Hg).

When using a phaco tip in accordance with the invention, the parameters of the aspiration/irrigation device preferably are as follows:

PARAMETERS
Phase One: Sculpting

|  | Normal Flow | Reverse Flow |
| --- | --- | --- |
| Machine power | 70% | 70% |
| Aspiration flow rate | 25 cc/min | 12–14 cc/min |
| Vacuum limit | 0 mm Hg | 100–110 mm Hg |
| Bottle Height above eye level | 70 cm | 70 cm |

Phase Two: Quadrant Removal

|  | Normal Flow |
| --- | --- |
| Machine power | 50–60% |
| Aspiration flow rate | 27 cc/min |
| Vacuum limit | 150 mm Hg |
| Bottle Height above eye level | 70 cm |

Reverse flow may also be used during phase two if residual nuclear or cortical material is adherent to the posterior capsule. In this case, a thin band of lens material is directly contacting the capsule and typically with normal flow the posterior capsule could be attracted to the vibrating tip and ruptured. Since aspiration takes place at the open end of the soft silicone sleeve and not at the phaco tip during reverse flow, fluid flow exiting the bore of the phaco tip tends to push the capsule away and thus helps to avoid direct tip contact, tip occlusion and subsequent posterior capsule rupture.

Reverse flow used during emulsification also has the effect of producing ultrasonic hydrodissection since the fluid exiting the hollow needle during emulsification is excited by the ultrasonic energy. The positive flow of this excited fluid helps to break cortical adhesions to the capsule and hydro delineate the nucleus.

The following table indicates the open "O" or closed "C" positions of the valves of FIG. 1:

| Valve | Valve Position "O" or "C" | | | | | |
| --- | --- | --- | --- | --- | --- | --- |
|  | 27 | 25 | 24a | 24b | 26a | 26b |
| Flow A | O | C | O | C | O | C |
| Flow B | O | C | C | O | C | O |

A = irrigate through needle 22
B = irrigate through annular space in sleeve 23

FIG. 2 illustrates another embodiment of the invention in which a suction pump 70 has two aspiration lines 70a, 70b and the treatment fluid supply 80 has two irrigation lines 80a, 80b. One aspiration line 70a and one irrigation line 80a branch off from a common line 120 that extends from a port of instrument 110. Further, the other aspiration line 70b and the other irrigation line 80b branch off from the common line 122 that extends from another port of instrument 110. At any given time, flow is permitted only through the aspiration line 70a and the irrigation line 80b or through the aspiration line 70b and the irrigation line 80a.

Such flow control may be effected with valves 130a, 130b, each in a respective one of the aspiration lines 70a, 70b, and with valves 140a, 140b, each in a respective one of the irrigation lines 80a, 80b. If valves 130a and 140b are open, then valves 130b and 140a are closed. If valves 130b and 140a are open, then valves 130a and 140b are closed. Valve opening and closure may be done manually, preferably with an interlock valve control system that only permits either of the aforementioned two conditions to arise.

By reversing the sources of irrigation and aspiration, such that irrigation is through the needle and aspiration is through the annular space between the needle and sleeve, emulsate is aspirated from the chamber. Under these conditions, it is almost impossible for the posterior capsule to be attracted to the vibrating phaco tip. In addition, the outflow of fluid from the phaco tip tends to push the posterior capsule back while at the same time decreasing cortical adherences due to enhanced continuous ultrasonic hydrodissection.

Reversal of flow in this manner may be continuous or intermittent. If intermittent, the flow may be controlled to revert back after a time delay (e.g., a few seconds) so that irrigation is through the annular space 116a between the needle and sleeve while aspiration is through the lumen of the needle.

The instrument 110 has a housing 112, an internal ultrasonic oscillation generator 114, a sleeve 116 and a tubular cutting tip 118. The protective sleeve 116 is tubular and is attached to the housing 112. The protective sleeve 116 is stationary with respect to the housing 112 and, once inserted in the eye, is also stationary with respect to the eye. The cutting tip 118 is positioned within the tubular protective sleeve 116 and is attached to a forward end of the ultrasonic oscillation generator 114, which reciprocates the cutting tip 118 along an axis A at a predetermined ultrasonic oscillation rate.

The common conduit 122 is in fluid communication with a tubular space 82 within needle 84 and the common conduit 120 is in fluid communication with an annular space 86 inside of housing 112, which in turn is in fluid communication with the annular spacing 116a within the protective sleeve 116.

Figure 3:
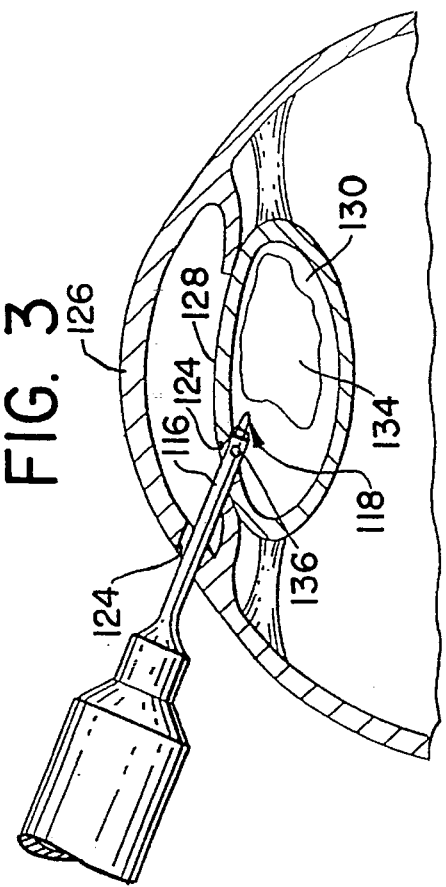
FIG. 3 is a partial cross-sectional side view of an eye showing the vibratory instrument including the cutting tip in an operational position.
Figure 4:
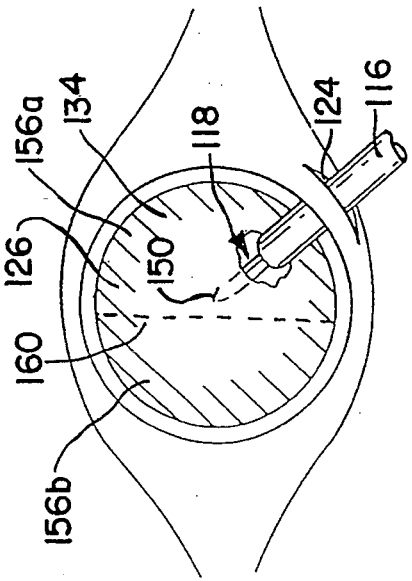
FIG. 4 is a front view of the eye of FIG. 3.

A small incision 124 is made in the cornea 126 and an opening 128 is made in the anterior wall of the capsular bag 130 using a scalpel or similar cutting instrument. Together, these two openings provide access to the interior of the capsular bag 130 through which the cutting tip of the vibratory instrument 110 is inserted by a surgeon, as shown in FIGS. 3 and 4. The protective sleeve 116 contacts the tissue of the cornea 126 adjacent the small incision 124. The protective sleeve 116 protects the healthy tissue (i.e., the tissue lying adjacent the incision 124) from the oscillating cutting tip 118 positioned therein and also provides one-way isolated fluid communication directly with the posterior capsule 130 through the annular space 116a between sleeve 116 and tip 118, for providing a passage for aspirating fluid from the surgical site. Two diametrically opposite radially extending holes or channels 136 are shown in FIG. 2 passing through the sleeve 116 to the outside. It is through these holes or channels 136 that the aspirating fluid reaches the annular space 116a from the outside. While two holes or channels 136 are preferred, additional holes or channels may also be provided to pass radially through the sleeve thickness.

The cutting tip 118 is positioned through the incision 124, but operates within the protective sleeve 116. A forwardmost portion 118a of the cutting tip 118 extends past the forward portion 132 of the protective sleeve 116 and into contact with the cataracted natural lens 134. This forward portion 132 is in sealing contact with the tip 118, spaced from the front edge 154 of the needle 84.

To break up the cataracted lens, the surgeon first inserts the tip 118 into the capsular bag 130. Once inserted, the surgeon uses the vibrating cutting tip 118 to make a shallow groove 160 (See FIG. 4) generally along the axis of the oscillation and near the center of the lens 134. The surgeon then elongates and deepens the groove until it extends across the lens 134 and almost completely therethrough. The groove 160 is made deeper by removing small amounts of cataracted tissue along the groove 160 until the lens 134 cracks into two more manageable half sections 156a, 156b.

In carving out the groove 160 (see FIG. 4), which is a process called "sculpting", the lens 134 becomes somewhat smaller in volume. The complete removal of the lens, however, still requires that each of the two half sections 156a, 156b be disintegrated. To disintegrate a half section in a controlled manner, the surgeon positions the cutting tip 118 against the section.

As the disintegration of tissue of the half section 156a continues, the vacuum from the aspiration of fluid continuously pulls the small particles of natural lens tissue in a rotation-like motion towards the vacuum. This has the effect of drawing fragmented portions of the lens that are farther away from the front surface 150 of the tip 118 toward the front surface 150 and the front edge 154 to be more effectively disintegrated at those surfaces. As the surgeon moves the tip 118 around the half section 156a of the lens, all of the disintegrated material is eventually removed. The surgeon can then disintegrate the opposite half 156b of the cataracted natural lens in the same manner.

Under conventional teaching, the aspiration is through the end of the cutting tip 118 while the irrigation is through the end of the annular space between the sleeve 116 and the cutting tip 118. In accordance with the present invention, the flow is reversible so that the irrigation may, at certain times during the procedure (i.e. whenever the front surface 150 of the tip 118 will be close to the posterior capsule) be accomplished through the cutting tip 118 while the aspiration is through the annular space 116a between the sleeve 116 and the cutting tip 118. Such flow reversal avoids attracting the posterior capsule to the phaco tip. If, as is conventionally the case, the opening through the needle is larger than the opening presented by the annular space between the needle and sleeve, it is preferred to reduce the flow volume when the flow is reversed in the manner according to the present invention. This may be done either by lowering the irrigation supply container, if it is a gravity feed system, and/or providing for a volumetric flow control valve in conduit 122 to regulate flow volume.

The following table indicates the open "O" or closed "C" position of the valves of FIG. 2:

| Valve | Valve Position "O" or "C" | | | |
| --- | --- | --- | --- | --- |
|  | 130a | 130b | 140a | 140b |
| Flow A | O | C | O | C |
| Flow B | C | O | C | O |

A = irrigate through annular space 116a in sleeve 116
B = irrigate through cutting tip 118

Within the meaning of the present invention, fluid aspiration means for aspirating fluid from the interior of the capsular bag to flow through the annular space includes any technique for aspirating, whether through the employment of an open system such as that of FIG. 1 that includes a gravity drain container 14 open to atmospheric pressure, or through a closed system such as that of FIG. 2 that includes a suction pump 70, or even through a system that relies on the ultrasonic oscillation of the tip 22 or 118 which, in effect, serves as a pump.

While the foregoing description and drawings represent the preferred embodiments of the present invention, it will be understood that various changes and modifications may be made without departing from the spirit and scope of the present invention.

What is claimed is:

1. A surgical instrument for aspirating and irrigating material within a capsular bag of an eye, comprising:

an elongated tube member having a distal end with a tip portion and a fluid conduit extending therethrough to a region of said tip;

a sleeve member surrounding said tube member in a direction of elongation of said tube member so as to define an annular space between said sleeve member and said tube member;

an irrigation fluid supply for supplying an irrigation fluid through said tube member to flow through said fluid conduit of said tube member to the region of the capsule to be aspirated;

fluid aspiration means for aspirating fluid from the interior of the capsular bag to flow through said annular space;

a first conduit joining said irrigation fluid supply with said fluid conduit of said tube member;

a first valve for opening and closing said first conduit;

a second conduit joining said fluid aspiration means with said annular space;

a second valve for opening and closing said second conduit;

a third conduit joining said irrigation fluid supply with said annular space;

a third valve for opening and closing said third conduit;

a fourth conduit joining said fluid aspiration means with said fluid conduit of said tube member;

a fourth valve for opening and closing said fourth conduit;

means for controlling said first, second, third, and fourth valves such that flow is permitted either through only said first and second conduits to irrigate through said tube member and aspirate through said annular space, or through only said third and fourth conduits to irrigate through said annular space and aspirate through said tube member.

2. A surgical instrument as in claim 1, further comprising means for imparting an oscillation movement to said distal end of said tube member.

3. A surgical instrument as in claim 1, further comprising reversing means for intermittently reversing the flows from through only said first and second conduits to through only said third and fourth conduits.

4. A method of aspirating and irrigating material within a capsular bag of an eye with a surgical instrument comprising an elongated tube member having a distal end with a tip and a fluid conduit extending through said tube member to said tip, said instrument further comprising a sleeve member disposed longitudinally about said tube member to define an annular space between said tube member and said sleeve member, said method comprising the steps of:

supplying an irrigation fluid through a first conduit and into said fluid conduit within said elongated tube member to flow, through said tip, to the region of the capsule to be aspirated;

aspirating fluid from the interior of the capsular bag to flow through said annular space into a second conduit and out to a drain container;

reversing the flows through said fluid conduit of said tube member and through said annular space such that irrigation occurs through a third conduit and into said fluid conduit of said tube member and aspiration occurs through said annular space into a fourth conduit and out to said drain container;

preventing flow through said third and fourth conduits while supplying irrigation fluid through said first conduit and aspirating fluid into said second conduit; and preventing flow through said first and second conduit while supplying irrigation fluid through said third conduit and aspirating fluid into said fourth conduit.

5. A method as in claim 4, further comprising the step of imparting an oscillation movement to said distal end of said tube member.

6. A method as in claim 4, wherein the step of reversing the flows includes intermittently reversing the flows including the step of cycling said step of reversing the flows on after a time delay and off after a duration of flow reversal has elapsed.

7. A method as in claim 1, further comprising a control means for automatically controlling opening and closing of said first, second, third, and fourth valves, said control means preventing said third and fourth valves from being open when said first and second valves are open and further preventing said first and second valves from being open when said third and fourth valves are open.

8. A method as in claim 1, further comprising an interlock valve control system for manually operating said first, second, third, and fourth valves, said control system preventing said third and fourth valves from being open when said first and second valves are open and further preventing said first and second valves from being open when said third and fourth valves are open.

9. An apparatus as in claim 3, further comprising means for cycling said reversing means on after a time delay and off after a duration of flow reversal has elapsed.

10. A method as in claim 4, further comprising the step of varying irrigation and aspiration flow rates upon reversing fluid flows to maintain safe inflation of the anterior chamber of the eye.

11. A method as in claim 10, further comprising the step of varying irrigation flow rate by varying the height of a gravity feed and gravity discharge apparatus that supplies irrigation fluid.

12. A method as in claim 10, further comprising the step of reducing the volumetric flow rate of the irrigation stream upon reversing said flows to irrigate through said fluid conduit of said tube member.

13. A method as in claim 12, further comprising the step of reducing the aspiration flow rate upon reversing said flows to aspirate through said annular space, thereby balancing flows in and out of the anterior chamber of the eye.

14. A method as in claim 10, wherein said step of varying irrigation and aspiration flow rates is determined by the relative dimensions of said tube member and said annular space.

* * * * *